(12) United States Patent
Tucker

(10) Patent No.: US 10,525,158 B2
(45) Date of Patent: Jan. 7, 2020

(54) ELECTROCHEMICAL SYSTEM FOR DISINFECTING AND CLEANING CONTACT LENSES

(71) Applicant: Novartis AG, Basel (CH)

(72) Inventor: Robert Carey Tucker, Suwanee, GA (US)

(73) Assignee: Novartis AG, Basel (CH)

( * ) Notice: Subject to any disclaimer, the term of this patent is extended or adjusted under 35 U.S.C. 154(b) by 379 days.

(21) Appl. No.: 15/300,301

(22) PCT Filed: Mar. 23, 2015

(86) PCT No.: PCT/US2015/021950
§ 371 (c)(1),
(2) Date: Sep. 29, 2016

(87) PCT Pub. No.: WO2015/153161
PCT Pub. Date: Oct. 8, 2015

(65) Prior Publication Data
US 2017/0173206 A1    Jun. 22, 2017

Related U.S. Application Data

(60) Provisional application No. 61/974,582, filed on Apr. 3, 2014.

(51) Int. Cl.
*A61L 12/10* (2006.01)
*A61L 12/08* (2006.01)
(Continued)

(52) U.S. Cl.
CPC .............. *A61L 12/00* (2013.01); *A61L 12/023* (2013.01); *A61L 12/08* (2013.01); *A61L 12/086* (2013.01);
(Continued)

(58) Field of Classification Search
CPC .............................. A61L 12/023; C02F 1/4674
See application file for complete search history.

(56) References Cited

U.S. PATENT DOCUMENTS

| 4,011,941 A | 3/1977 | Parsons |
| 4,585,488 A | 4/1986 | Giefer |

(Continued)

FOREIGN PATENT DOCUMENTS

| EP | 0124461 A1 | 11/1984 |
| GB | 1484945 | 9/1977 |

(Continued)

OTHER PUBLICATIONS

International Search Report and Written Opinion of the International Searching Authority, dated Jun. 5, 2015, International Application No. PCT/US2015/021946, International Filing Date: Mar. 23, 2015; 10 Pages.

(Continued)

*Primary Examiner* — Salil Jain
(74) *Attorney, Agent, or Firm* — Jian Zhou

(57) ABSTRACT

The present invention is generally related to a lens care system and method for disinfecting and cleaning contact lenses. A lens care system or method of the invention is based on electrolysis of an aqueous chloride solution for generating germicide species (e.g., chlorine, hypochlorous acid, hypochlorite, or combinations thereof) and subsequent in-situ electrolysis of hypochlorous acid or hypochlorite in the aqueous solution for neutralizing the generated germicide species.

10 Claims, 5 Drawing Sheets

(51) Int. Cl.
  *A61L 12/00*   (2006.01)
  *C02F 1/467*   (2006.01)
  *A61L 12/02*   (2006.01)
  *A61L 12/14*   (2006.01)
  *C11D 3/00*    (2006.01)

(52) U.S. Cl.
  CPC .............. *A61L 12/10* (2013.01); *A61L 12/14* (2013.01); *C11D 3/0078* (2013.01); *C02F 1/4674* (2013.01)

(56) References Cited

U.S. PATENT DOCUMENTS

| | | | |
|---|---|---|---|
| 4,637,919 A | 1/1987 | Ryder | |
| 4,748,992 A | 6/1988 | Giefer | |
| 4,750,610 A | 6/1988 | Ryder | |
| 4,776,360 A | 10/1988 | Ching | |
| 4,812,173 A | 3/1989 | Tsao | |
| 4,816,232 A | 3/1989 | Barrau | |
| 4,836,859 A | 6/1989 | Konishi | |
| 4,852,591 A | 8/1989 | Wisotzki | |
| 4,889,689 A | 12/1989 | Tsao | |
| 4,899,914 A | 2/1990 | Schweigl | |
| 4,956,156 A | 9/1990 | Kanner | |
| 4,986,290 A | 1/1991 | Oguma | |
| 4,996,027 A | 2/1991 | Kanner | |
| 5,011,661 A | 4/1991 | Schäfer | |
| 5,089,240 A | 2/1992 | Perlaky | |
| 5,117,849 A | 6/1992 | Zimmerli | |
| 5,129,999 A * | 7/1992 | Holland | A45C 11/005 204/194 |
| 5,196,174 A * | 3/1993 | Cerola et al. | |
| 5,225,055 A | 7/1993 | Sibley | |
| 5,250,266 A | 10/1993 | Kanner | |
| 5,252,291 A | 10/1993 | Tsao | |
| 5,256,268 A * | 10/1993 | Goto | C02F 1/46109 204/255 |
| 5,270,002 A * | 12/1993 | Neff et al. | |
| 5,275,784 A | 1/1994 | Perlaky | |
| 5,302,345 A | 4/1994 | Oksman | |
| 5,312,586 A | 5/1994 | Stockel | |
| 5,314,590 A | 5/1994 | Kamiya | |
| 5,320,806 A | 6/1994 | Dziabo | |
| 5,449,442 A | 9/1995 | Yamada et al. | |
| 5,451,303 A | 9/1995 | Heiler | |
| 5,462,713 A | 10/1995 | Schlitzer | |
| 5,468,448 A | 11/1995 | Nicolson | |
| 5,487,788 A | 1/1996 | Kamiya | |
| 5,523,012 A | 6/1996 | Winterton | |
| 5,558,846 A | 9/1996 | Alvord | |
| 5,576,028 A | 11/1996 | Martin | |
| 5,591,397 A | 1/1997 | Schlitzer | |
| 5,609,264 A | 3/1997 | Cerny | |
| 5,609,837 A | 3/1997 | Cerny | |
| 5,807,585 A | 9/1998 | Martin | |
| 5,958,351 A | 9/1999 | Cerny | |
| 6,183,705 B1 | 2/2001 | Chang | |
| 6,440,411 B2 | 8/2002 | Scherer | |
| 6,945,389 B2 | 9/2005 | Scherer | |
| 7,022,654 B2 | 4/2006 | Tsao | |
| 8,318,144 B2 | 11/2012 | Ketelson | |
| 8,329,098 B2 | 12/2012 | Kanner | |
| 2006/0151326 A1* | 7/2006 | Koizumi | G21C 19/46 205/43 |
| 2008/0276971 A1 | 11/2008 | Ifejika | |
| 2009/0136598 A1* | 5/2009 | Chapin | A61K 9/0048 424/680 |
| 2010/0233023 A1 | 9/2010 | Kanner | |
| 2011/0010835 A1* | 1/2011 | McCague | C02F 1/4674 4/494 |
| 2011/0114517 A1 | 5/2011 | Minick | |
| 2012/0152284 A1 | 6/2012 | Winterton | |
| 2012/0205255 A1* | 8/2012 | Roster | A61L 12/023 205/626 |
| 2012/0211027 A1* | 8/2012 | Francavilla et al. | |
| 2013/0008354 A1* | 1/2013 | Constantz | C04B 14/26 106/801 |
| 2014/0158623 A1* | 6/2014 | Pudil | A61M 1/1656 210/647 |

FOREIGN PATENT DOCUMENTS

| | | |
|---|---|---|
| GB | 1484972 | 9/1977 |
| GB | 2094992 A | 9/1982 |
| JP | 2286163 A | 11/1990 |
| JP | H09154922 A | 6/1997 |
| JP | 2669690 B2 | 10/1997 |
| JP | 3174882 U | 4/2012 |
| WO | 9534327 A1 | 12/1995 |
| WO | 2013056165 A1 | 4/2013 |

OTHER PUBLICATIONS

Celine Coulon, Anne Collignon, Gerald McDonnell and Vincent Thomas, Resistance of Acanthamoeba Cysts to Disinfection Treatments Used in Health Care Settings, Journal of Clinical Microbiology, 2010, vol. 48, No. 8, pp. 2689-2697.

L. Czarnetzki and L. J. J. Janssen, Electrochemical Oxidation of Hypochlorite at Platinum Anodes, Electrochimica Acta., 1988, vol. 33, No. 4, pp. 561-566.

L. R. Czarnetzki and L. J. J. Janssen, Formation of hypochlorite, chlorate and oxygen during NaCl electrolysis from alkaline solutions at an RuO2/TiO2 anode, Journal of Applied Electrochemistry, 1992, vol. 22, pp. 315-324.

Reanne Hughes and Simon Kilvington, Comparison of Hydrogen Peroxide Contact Lens Disinfection Systems and Solutions against Acanthamoeba polyphaga, Antimicrobial Agents and Chemotherapy, 2001, vol. 45, No. 7, pp. 2038-2043.

Stephanie P. Johnston, Rama Sriram, Yvonne Qvarnstrom, Sharon Roy, Jennifer Verani, Jonathan Yoder, Suchita Lorick, Jacquelin Roberts, Michael J. Beach and Govinda Visvesvara, Resistance of Acanthamoeba Cysts to Disinfection in Multiple Contact Lens Solutions, Journal of Clinical Microbiology, 2009, vol. 47, No. 7, pp. 2040-2045.

N. Krstajic, V. Nakic, M. Spasojevic, Hypochlorite Production. I. A model of the cathodic reactions, Journal of Applied electrochemistry, 1987, vol. 17, pp. 77-81.

Yoshiharu Mukouyama, Shuji Nakanishi, Hidemitsu Konishi, Kouhei Karasumi and Yoshihiro Nakato, Observation of two stationary states of low and high H2O2-reduction currents at a Pt electrode, arising from the occurrence of a positive feedback mechanism including solution-stirring by gas evolution, Phys. Chem. Chem. Phys., 2001, vol. 3, pp. 3284-3289.

S Patra and N Munichandraiah, Electrochemical reduction of hydrogen peroxide on stainless steel, J. Chem. Sci., 2009, vol. 121, No. 5, pp. 675-683.

\* cited by examiner

ELECTROCHEMICAL SYSTEM FOR DISINFECTING AND CLEANING CONTACT LENSES

This invention relates generally to a lens care system and a method for disinfecting contact lenses.

BACKGROUND OF THE INVENTION

Contact lenses provide a means for vision correction for a wide range of consumers. The advantages of contact lens wear are numerous. Improved convenience and improved appearance in comparison to spectacle glasses are probably the two most important advantages to most consumers. However, contact lenses require stringent care regimes in order to ensure comfort and avoid ocular infections. Proper care of contact lenses typically requires the consumer to periodically clean and disinfect the lenses, to prevent infection or other deleterious effects on ocular health which may be associated with contact lens wear.

One lens care system is the use of multiple-purpose solutions to clean, to disinfect, and to rinse contact lenses. These systems typically comprise a small amount of one or more antimicrobial agents and have been dominating most of the lens care market. Such popularity is most likely derived from the easiness and convenience provided by these new systems to consumers. In order to achieve a satisfactory disinfecting result, a contact lens has to be in a multiple-purpose solution for a sufficient time period. But, patients do not have a direct way to determine if their lenses have been in the lens care solution long enough to disinfect the lenses. In addition, currently available multi-purpose lens care solutions have little efficacy toward organisms like *Acanthameoba*, the species of which can cause keratitis, a painful vision-threatening infection of the cornea, and fatal granulomatous encephalitis in humans.

Another lens care system is hydroge peroxide-based lens care systems, for example, as described in patents and patent applications, such as, U.S. Pat. Nos. 4,585,488, 4,748,992, 4,899,914, 5,011,661, 6,440,411, 5,089,240, 5,196,174, 5,275,784, 5,468,448, 5,558,846, 5,609,264, 5,609,837, 5,958,351, 6,945,389, 4,812,173, 4,889,689, 5,523,012, 5,576,028, 5,807,585, 5,462,713, 5,591,397, 5,312,586, US 2011/0114517, and EP0124461 (herein incorporated by references in their entireties). However, hydrogen peroxide in these lens care systems is toxic to the cornea and thereby must be neutralized before lenses can safely be worn by a patient. Hydrogen peroxide typically is neutralized by adding a catalyst either during the disinfection process (i.e., one-step involving use of a platinum-coated disk or soluble catalase tablet) or afterward (i.e., two-step involving the addition of a catalase or a reducing agent after a designated disinfection time). The study of Hughes and Kilvington indicated that the commercially available hydrogen peroxide-based, one-step lens care systems has low or no activity against the cysts of *Acanthamoeba* species under study because of insufficient exposure time, whereas the commercially available two-step systems can have at least a 3-log kill after 4 hours of exposure (R. Hughes & S. Kilvington, "Comparison of Hydrogen Peroxide Contact Lens Disinfection Systems and Solutions against *Acanthamoeba polyphaga*," Antimicrobial Agents and Chemotherapy, vol. 45, no. 7, pp. 2038-2043, July 2001). However, one disadvantage associated with the use of a two-step system is that a patient may inadvertently fail to neutralize hydrogen peroxide or prematurely remove lenses from the system, thereby suffering pain and trauma caused by hydrogen peroxide introduced into the eye.

Other methods for cleaning/disinfecting contact lenses have been reported that involve use of oxidizing agents and different neutralizing mechanisms.

For example, U.S. Pat. Nos. 5,462,713 and 5,591,397A describe a method for rapid disinfection of contact lenses, based on the combination of an oxidizing agent (i.e. peroxide, hypochlorite, ora precursor thereof) and a reducing agent (e.g., potassium iodide) and a neutralizing agent (e.g., ascorbate) for neutralizing Iodine generated through the reaction between the oxidizing agent and the potassium iodide.

U.S. Pat. No. 5,312,586 describes a method for rapid disinfection of contact lenses, based on using a peroxygen or hypochlorite compounds to disinfect the lenses and subsequently using active carbon to deactivate the peroxide or hyperchlorite.

GB2094992A describes a method for disinfecting contact lenses, based on hypochlorites generated through an electrical current and subsequently neutralized by its slow reaction with oxygen over a long period of time (e.g., overnight) or by using a platinum catalyst or a reducing agent in a short period of time.

GB1484972A describes a method for disinfecting contact lenses, which comprises contacting a contact lens with a solution including hypochlorite ions in an amount effective to kill pathogenic microorganisms and thereafter reducing all the hypochlorite to chloride with a reducing agent (e.g., sodium thiosulfate). The method of GB1484972 can be performed by using a tablet consisting of a top layer comprising a hypochlorite salt (i.e. sodium hypochlorite) and a bottom layer surrounded by gelatin and comprising a reducing agent (e.g., sodium thiosulfate) which is released after a certain time (e.g., about 30 minutes) needed for disintegrating the gelatin.

U.S. Pat. No. 5,451,303 describes a method for cleaning and disinfecting of contact lenses that involves placing a contaminated lens between an electrochemical oxidant-reductant pair (e.g., one being an oxidant in a gel and the other being a reductant contained in another gel) that have different oxidation potentials that generate an electrochemical potential difference across the lens sufficient to cause charged deposits to be removed from the lens.

JP2669690B2 describes a method for cleaning and sterilizing contact lenses which involves immersing a contact lens in an electrolytic solution which does not generate a hypochlorite by electrolysis and passing a DC current through the electrolyte solution so as to remove proteins and microorganisms.

EP0124461A1 describes a method that involves placing the lens in a solution an oxidant (e.g., hydrogen peroxide) to kill microorganisms, then placing in a second agent (e.g., hypochlorite or dichloroisocyanurate), which will degrade into products that are harmless for the eye.

WO 2013056165 describes a complicated lens cleaning system which functions as a two-step hydrogen peroxide system while, for the user, it functions as a one-step system. A system of WO 2013056165 comprises a reservoir for holding a hydrogen peroxide solution, a complex base that is coupled to the reservoir to insure a hermetically closed reservoir environment and has a first and a second segment, a lens holder assembly configured to locate and releasably coupled lenses within the reservoir and being coupled to the first segment, and a drive mechanism being coupled to the second segment and configured to selectively introduce a catalyst to the hydrogen peroxide solution.

US2012/0205255 describes an ozone-generating apparatus and use thereof for disinfecting contact lenses.

U.S. Pat. No. 5,252,291 described a device and method for cleaning and disinfecting contact lenses according to the principles of electrophoresis and electrolysis. A device of U.S. Pat. No. 5,252,291 comprises a contact lens containing well with two well electrodes spaced apart from each other for inserting one or two contact lens or lenses therebetween and a reservoir having one reservoir electrode and connected to the contact lens containing well via a narrow channel. In operation, for disinfecting contact lenses chlorine is generated electrolytically from chloride in the contact lens containing well by the generation of an electrical field between the two electrodes, and then the chlorine is removed from the contact lens containing well while being generated in the reservoir, by generating an electrical field between the well electrodes and the electrode in the reservoir. It was believed that the chlorine formed in the reservoir would have a long diffuse path across the ion permeable bridge, minimizing reintroducing the chlorine in the lens containing well. However, this patent does not disclose how much chlorine is produced at different times and how fast the chlorine is removed.

There is still a need for a simple lens care systems which can have microbial efficacy toward a broad spectrum of organisms including *Acanthameoba*.

SUMMARY OF THE INVENTION

The present invention is related to a lens care system (apparatus) for disinfecting contact lenses. The system (apparatus) of the invention comprises: (1) a container for holding an aqueous lens care solution having a pH of from about 6 to about 8 (preferably from about 6.5 to about 7.5, more preferably from about 6.8 to about 7.2) and comprising from about 0.30% to about 1.4% (preferably from about 0.5% to about 1.2%, more preferably from about 1.0%) by weight of one or more halide salts (e.g., sodium chloride, potassium chloride, sodium bromide, potassium bromide, sodium iodide potassium iodide, or mixtures thereof), preferably chloride salts (e.g., sodium chloride, potassium chloride or both) and a tonicity of from about 150 to about 400 mOsm/kg (preferably from about 200 to about 350 mOsm/kg, more preferably from about 250 to about 350 mOsm/kg) at 25° C., wherein the container comprises a container cup defining an interior chamber accessible through an opening bounded by a rim and for receiving the aqueous lens care solution, a cap for removable attachment onto the container cup to cover the opening, and a lens holder for retaining the contact lenses immersed in the aqueous lens care solution in the container cup; (2) a set of electrodes which are located in the interior chamber and immersed in the aqueous lens care solution when in use, wherein the set of electrodes comprises a first anode free of any negatively-charged membrane thereon, a second anode having a negatively charged membrane thereon for preventing a negatively charged ion from accessing the second anode, a first cathode, and optionally a second cathode; and (3) and a control unit operatively connected to the set of electrodes and to a power source, wherein the control unit automatically applies a first potential between the first anode and the first cathode and drives an electrical current through the first anode and the first cathode for a first period of time to electrochemically generate germicide species including halogen (e.g., chlorine, bromine or iodine, preferably chlorine), hypohalous acid (e.g., hypochlorous acid, hypobromous acid or hypoiodous acid, preferably hypochlorous acid), hypohalorite (e.g., hypochlorite, hypobromite or hypoiodite, preferably hypochlorite), or combinations thereof for disinfecting the contact lenses, and after the first period of time and optionally a disinfecting period of time for disinfecting contact lenses with the electrochemically generated germicide species, automatically applies a second potential between the second anode and the first or second cathode and drives an electrical current through the second anode and the first or second cathode for a second period of time to electrochemically neutralizing germicide species which are generated electrochemically but left-over from disinfecting of the contact lenses.

The present invention is also related to a method for disinfecting and cleaning contact lenses which are suitable for direct insertion into the eye upon completion of disinfection. A method of the invention comprises the steps of: (1) immersing a contact lens in an aqueous lens care solution including which comprises from about 0.30% to about 1.4% (preferably from about 0.5% to about 1.2%, more preferably from about 0.7% to about 1.0%) by weight of one or more chloride salts (e.g., sodium chloride, potassium chloride, or both) and has a pH of from about 6 to about 8 (preferably from about 6.5 to about 7.5, more preferably from about 6.8 to about 7.2) and a tonicity of from about 150 to about 400 mOsm/kg (preferably from about 200 to about 350 mOsm/kg, more preferably from about 250 to about 350 mOsm/kg) at 25° C.; (2) electrochemically generating germicide species in the aqueous lens care solution by using a first anode and a first cathode for a first period of time for disinfecting the contact lenses; (3) after the first period of time and optionally a disinfecting period of time, electrochemically neutralizing the germicide species which are generated electrochemically in step (2) and left-over from disinfecting of the contact lenses in the aqueous lens care solution, wherein the step of electrochemically neutralizing the germicide species is carried out by using a second anode and the first cathode or a second cathode, wherein the second anode has a negatively-charged membrane thereon for preventing a negatively charged ion from accessing the second anode.

The present invention provides the foregoing and other features, and the advantages of the invention will become further apparent from the following detailed description of the example embodiments set forth herein, read in conjunction with the accompanying figures. The detailed description and figures are merely illustrative of the invention and do not limit the scope of the invention, which is defined by the appended claims and equivalents thereof.

DETAILED DESCRIPTION OF EMBODIMENTS OF THE INVENTION

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well-known and commonly employed in the art. Also, as used in the specification including the appended claims, reference to singular forms such as "a," "an," and "the" include the plural, and reference to a particular numerical value includes at least that particular value, unless the context clearly dictates otherwise. "About" as used herein means that a number referred to as "about" comprises the recited number plus or minus 1-10% of that recited number.

This invention is generally related to a lens care system and method for disinfecting and cleaning contact lenses. A lens care system or method of the invention is based on electrolysis of an aqueous chloride solution for generating germicide species including halogen (e.g., chlorine, bromine or iodine, preferably chlorine), hypohalous acid (e.g., hypochlorous acid, hypobromous acid or hypoiodous acid, preferably hypochlorous acid), hypohalorite (e.g., hypochlorite, hypobromite or hypoiodite, preferably hypochlorite), or combinations thereof and subsequent in-situ electrolysis of germicide species in the aqueous solution for neutralizing the generated germicide species.

Figure 1:
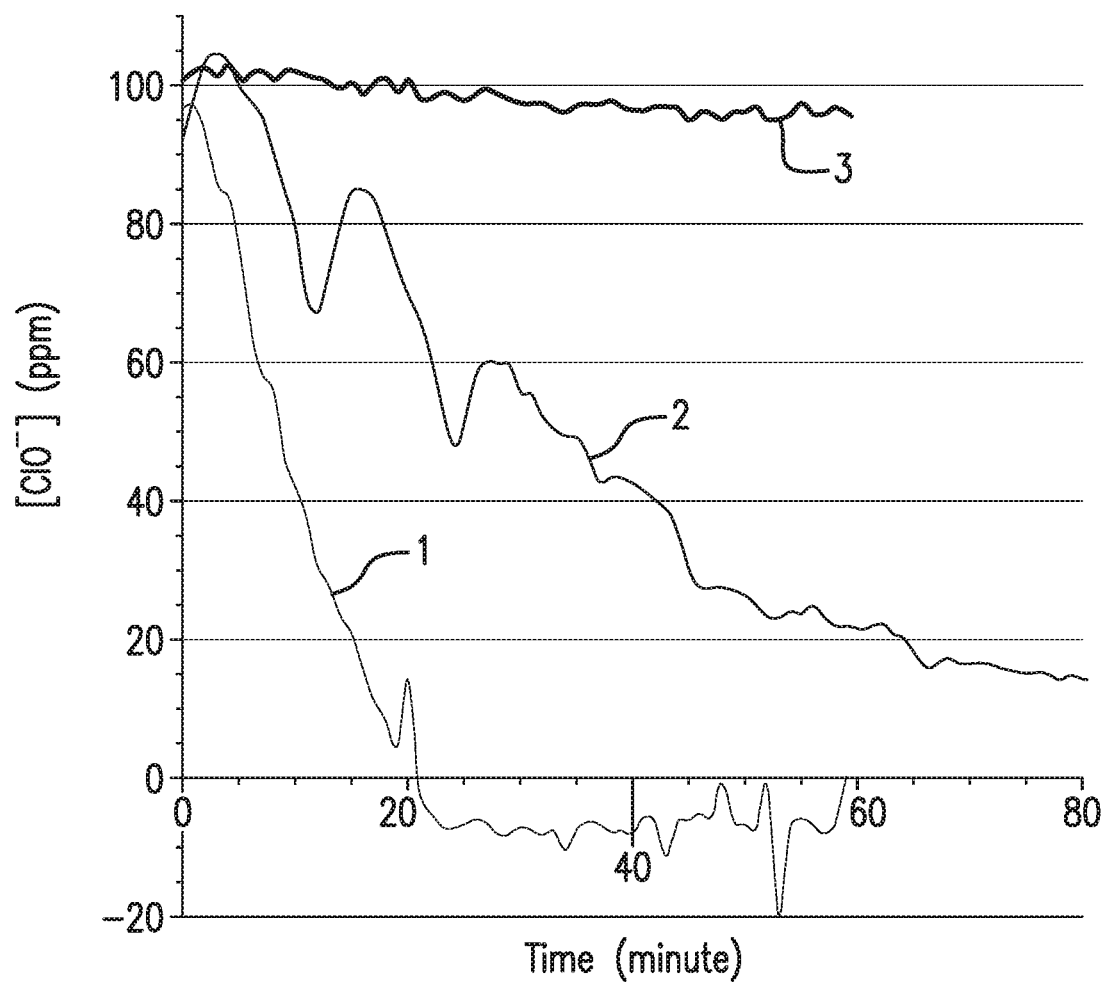
FIG. 1 shows the efficiencies of three systems in reducing 100 ppm hypochlorite solution: Curve 1 by an electrolysis system comprising an anode having limited or non-accessibility by anion is used in combination with a cathode; Curve 2 by an electrolysis system comprising two bare platinum electrodes.

The invention is partly based on the discovery that when an anode having limited or non-accessibility by anion is used in combination with a cathode in electrolysis of hypochlorous acid or hypochlorite in a solution, the level of hypochlorite and/or hypochlorous acid can be reduced well below 1 ppm (i.e., the on-eye safety limit) after a desired period of time for disinfecting contact lenses with hypochlorous acid and/or hypochlorite (see FIG. 1, Curve 1). In contrast, when a bare platinum electrode (i.e., fully accessible by anions) is used as known in the art, hypochlorous acid or hypochlorite cannot be fully removed and the level of hypochlorous acid or hypochlorite remains greater than 10 ppm, well above the on-eye safety limit, even after 80 minutes of electrolysis (FIG. 1, Curve 2).

A lens care system of the invention comprises a pair of electrodes (such as, two bare platinum electrodes, one as the anode and the other as the cathode) for electrochemically generating germicide species (e.g., chlorine, hypochlorous acid, hypochlorite, or combinations thereof). Chlorine is formed at anode ($2Cl^- \rightarrow Cl_2 + 2e^-$); hydrogen is formed at cathode ($2H_2O + 2e^- \rightarrow H_2 + 2OH^-$). Hypochlorous acid and hypochlorite are formed in disproportionation reaction of chlorine

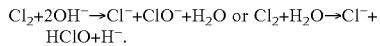

A lens care system of the invention must also comprise a second pair of electrodes consisting of a cathode (which can be the cathode of the first pair of electrodes) and an anion-inaccessible anode (i.e., an anode having a negatively-charged membrane thereon for preventing a negatively charged ion from accessing the anode) for electrochemically neutralizing remaining germicide species left-over after disinfecting contact lenses at cathode. Because of use of an anode with no accessibility by anions (e.g., chloride), no or minimal formation of chlorine can occur during electrolysis of hypochlorous acid or hyperchlorite. The half reaction at anode will be the formation of oxygen from water ($2H_2O \rightarrow O_2 + 4H^+ + 4e^-$).

One of the advantages of this system is that hypochlorite can be allowed to disinfect lenses for any desired period of time so as to kill even resistant cyst form of *Acanthamoeba* and then conveniently neutralized electrochemically. It has been reported that sodium hypochlorite solutions with 2.5% concentration were found to completely kill multiple *Acanthamoeba* cyst strains in as little as 10 minutes, while more dilution solutions (0.25%) were found to completely kill most strains in 30 minutes (see, C. Coulon, A. Collignon, G. McDonnell, and V. Thomas, "Resistance of *Acanthamoeba* cysts to disinfection treatments used in health care settings," Journal of clinical microbiology, vol. 48, no. 8, pp. 2689-97, August 2010). Once a desired period of time for disinfection is complete, then a current can be applied to a pair of electrodes (e.g., platinum electrodes) which electrochemically neutralize hypochlorite into chloride.

Another advantage of this system is its simplicity, high controllability, ease of implementation, and relatively low cost, because it is based on a simple electrochemistry and can be implemented and controlled by using three electrodes or two pairs of electrodes, a power source and a control means (microelectronics) for turning-on and off the electric current. Alternatively, the neutralization reaction can either occur in the lens case container, or be pumped into a reaction vessel where the best reaction conditions (i.e. exposed to a catalyst, heated, ideal electrode positioning and area) can be used.

A further advantage of this system is that any known lens care solutions can be used in this system, so long as it contains chloride ions.

A lens care system of the invention can be used to disinfect any contact lenses including hard (PMMA) contact lenses, soft (hydrophilic) contact lenses, and rigid gas permeable (RGP) contact lenses. The soft contact lenses are hydrogel contact lens or silicone hydrogel contact lenses.

A "hydrogel" refers to a polymeric material which can absorb at least 10 percent by weight of water when it is fully hydrated. Generally, a hydrogel material is obtained by polymerization or copolymerization of at least one hydrophilic monomer in the presence or absence of additional monomers and/or macromers.

A "silicone hydrogel" refers to a hydrogel obtained by copolymerization of a polymerizable composition comprising at least one silicone-containing vinylic monomer or at least one silicone-containing macromer.

"Hydrophilic," as used herein, describes a material or portion thereof that will more readily associate with water than with lipids.

For the purposes of the present invention the term "disinfect" means the rendering non-viable of substantially all pathogenic microorganisms including *Acanthameoba*.

The present invention, in one aspect, provides a lens care system for disinfecting contact lenses. The system of the invention comprises: (1) a container for holding an aqueous lens care solution having a pH of from about 6 to about 8 (preferably from about 6.5 to about 7.5, more preferably from about 6.8 to about 7.2) and a tonicity of from about 150 to about 400 mOsm/kg (preferably from about 200 to about 350 mOsm/kg, more preferably from about 250 to about 350 mOsm/kg) at 25° C. and comprising from about 0.30% to about 1.4% (preferably from about 0.5% to about 1.2%, more preferably from about 0.7 to about 1.0%) by weight of one or more halide salts (e.g., sodium chloride, potassium chloride, sodium bromide, potassium bromide, sodium iodide potassium iodide, or mixtures thereof), preferably chloride salts (e.g., sodium chloride, potassium chloride, or both), wherein the container comprises a container cup defining an interior chamber accessible through an opening bounded by a rim and for receiving the aqueous lens care solution, a cap for removable attachment onto the container cup to cover the opening, and a lens holder for retaining the contact lenses immersed in the aqueous lens care solution in the container cup; (2) a set of electrodes which are located in the interior chamber and immersed in the aqueous lens care solution when in use, wherein the set of electrodes comprises a first anode free of any negatively-charged membrane thereon, a second anode having a negatively charged membrane thereon for preventing a negatively charged ion from accessing the second anode, a first cathode, and optionally a second cathode; and (3) and a control unit operatively connected to the set of electrodes and to a power source, wherein the control unit automatically applies a first potential between the first anode and the first cathode and drives an electrical current through the first anode and the first cathode for a first period of time to electrochemically generate germicide species including halogen (e.g., chlorine, bromine or iodine, preferably chlorine), hypohalous acid (e.g., hypochlorous acid, hypobromous acid or hypoiodous acid, preferably hypochlorous acid), hypohalorite (e.g., hypochlorite, hypobromite or hypoiodite, preferably hypochlorite), or combinations thereof for disinfecting the contact lenses, and after the first period of time and optionally a disinfecting period of time for disinfecting contact lenses with the electrochemically generated germicide species, automatically applies a second potential between the second anode and the first or second cathode and drives an electrical current through the second anode and the first or second cathode for a second period of time to electrochemically neutralizing germicide species which are generated electrochemically but left-over from disinfecting of the contact lenses.

Any containers known to person skilled in the art can be used in the invention. Containers used in lens care systems, especially in hydrogen peroxide-based lens care systems, are known in the art, and examples are provided in U.S. Pat. Nos. 4,011,941, 4,637,919, 4,750,610, 4,956,156, 4,966,027, 5,089,240, 5,196,174, 5,250,266, 5,275,784, 5,468,448, 5,558,846, 5,609,264, 5,609,837, 5,958,351, 6,945,389, 8,329,098 and US published patent application No. 2012/0152284 A1, the disclosures of which are incorporated herein by references in their entireties. The contact lens containers utilized in such lens care systems typically comprise closable baskets, which open to receive the contact lenses to be cleaned and close to retain the lenses during treatment. The baskets are typically part of a contact lens holder component, which in turn can be connected to the cap of a contact lens container. Before the cap is placed onto the container cup, the container cup is dosed to a fill level with a hydrogen peroxide lens care solution. Finally, the contact lens holder containing the lenses to be treated is immersed into the lens care solution in the container cup, and the container is closed by screwing the cap onto the container cup. The closure of the cap on the container cup may form a water-tight seal, to prevent leakage of the cleaning solution. The contact lenses are allowed to remain immersed in the solution for a period of time sufficient to complete the specified cleaning and/or disinfecting process. The hydrogen and oxygen produced from decomposition of water in the solution during electrolysis typically must be allowed to discharge from the container in some manner, e.g., according to one of various known gas discharge mechanisms, such as those disclosed in U.S. Pat. Nos. 4,011,941, 4,637,919, 4,750,610, 4,956,156, 4,966,027, 5,196,174, 5,250,266, 5,558,846, 5,609,264, 5,609,837, 5,958,351, 6,945,389, 8,329,098 and US published patent application No. 2012/0152284 (incorporated herein by reference in their entireties).

Containers known in the art can be modified to contain the set of electrodes. In accordance with the invention, a lens care system comprises: one anion-accessible anode (i.e., a first anode); one anion-inaccessible anode (i.e., a second anode having a negatively charged membrane thereon for preventing a negatively charged ion from accessing the second anode); a first cathode; and optionally a second cathode. It is understood that the first cathode can also function as the second cathode, i.e., the second cathode can be eliminated from the system. All the electrodes used in the invention by their very nature are electrically conductive, and in operation an electrical current can be driven through each of them to and from the power source. In accordance with the invention, the electrodes are comprised of a conventional inert electrically conductive material, e.g. platinum, graphite, palladium, aluminum, gold, silver, ruthenium, or boron doped diamond, a conductive polymer, or any conductive material known to a person skilled in the art. Each electrode, especially the first anode and the first cathode, can be made of mesh of an electrically conductive material to increase its surface area for electrolysis reaction, or alternatively the first anode and the first cathode are made of mesh of an electrically conductive material and are applied to the inside walls near the bottom of the interior chamber of the cup of a container. Various diamond electrodes are disclosed in US 2012/0205255 (herein incorporated by reference in its entireties).

The second anode (i.e., the anion-inaccessible anode) comprises a negatively charged membrane thereon (e.g., Nafion, or the like) for preventing a negatively charged ion from accessing the second anode. This electrode needs to be coated with a Nafion membrane (say with a dip and solvent evaporation step) or separated from a solution with a negatively charged membrane. Such an anion-inaccessible anode can be prepared by dipping an electrode in an organic solution of a negatively-charged material and then evaporating organic solvent to form an negatively-charged membrane on the surface of the electrode. Such a negatively charged membrane allows only neutral or cations (i.e., positively charged ions) to pass through to reach the surface of the anode. Any chloride ions would be rejected, but allowing free transport of sodium ions and neutral water molecules. This would allow the formation of oxygen and hydroxyl ions at the anode, instead of forming chlorine (subsequently hypochlorous acid and hypochlorite) from the chloride ions. Meanwhile, chlorine or hypochlorites would be reduced at the first or second cathode.

The contact lens care system of the present invention also includes a control unit (means), operatively connected to the electrodes and to a power source. The control unit permits the control of the polarity of each electrode and the amount of potential voltage applied to each electrode. Preferably the control unit is automatic and controls the electrode polarity and potential voltage according to a predetermined program. Preferably, the control unit also includes means (e.g., one or more miniaturized electronic devices, such as microprocessors and/or embedded systems, as known to a person skilled in the art) for automatically controlling the electrode polarity and potential of the electrodes, as well as the timing and duration of the electrochemical neutralization process, so that the optimum disinfection and cleaning efficacy is obtained. The control unit may optionally contain a power pack (AC or DC battery), an automatic switching mechanism, indicator means, etc.

The lens care system may be designed so that it is turned on by the user using a hand-operated switching device. Alternatively, the system may be automatically activated, for example, upon closing (attaching) of the container cap onto the container cup.

Figure 2A:
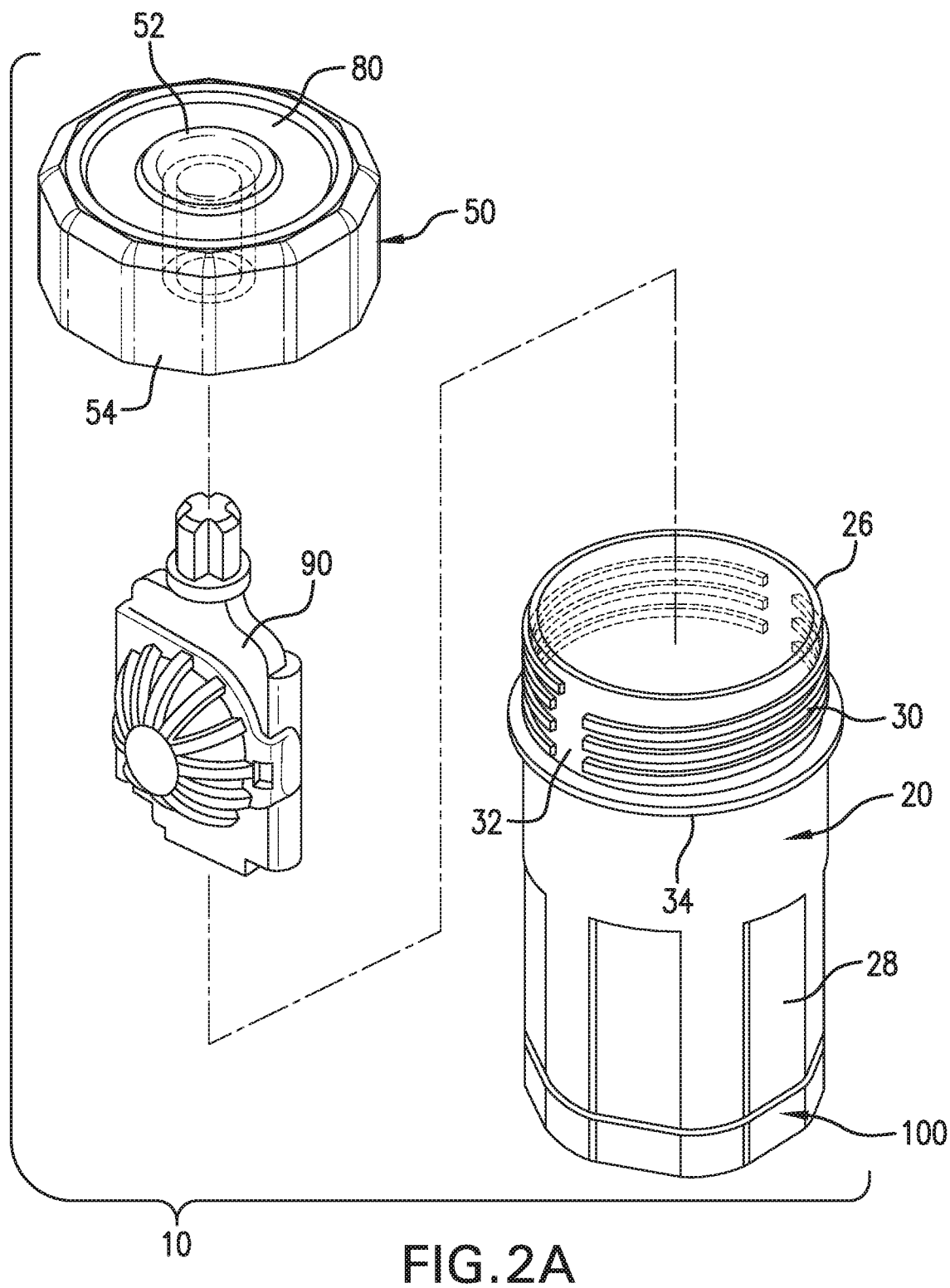
FIG. 2A is an assembly view of a lens care system according to a preferred embodiment of the present invention.
Figure 2B:
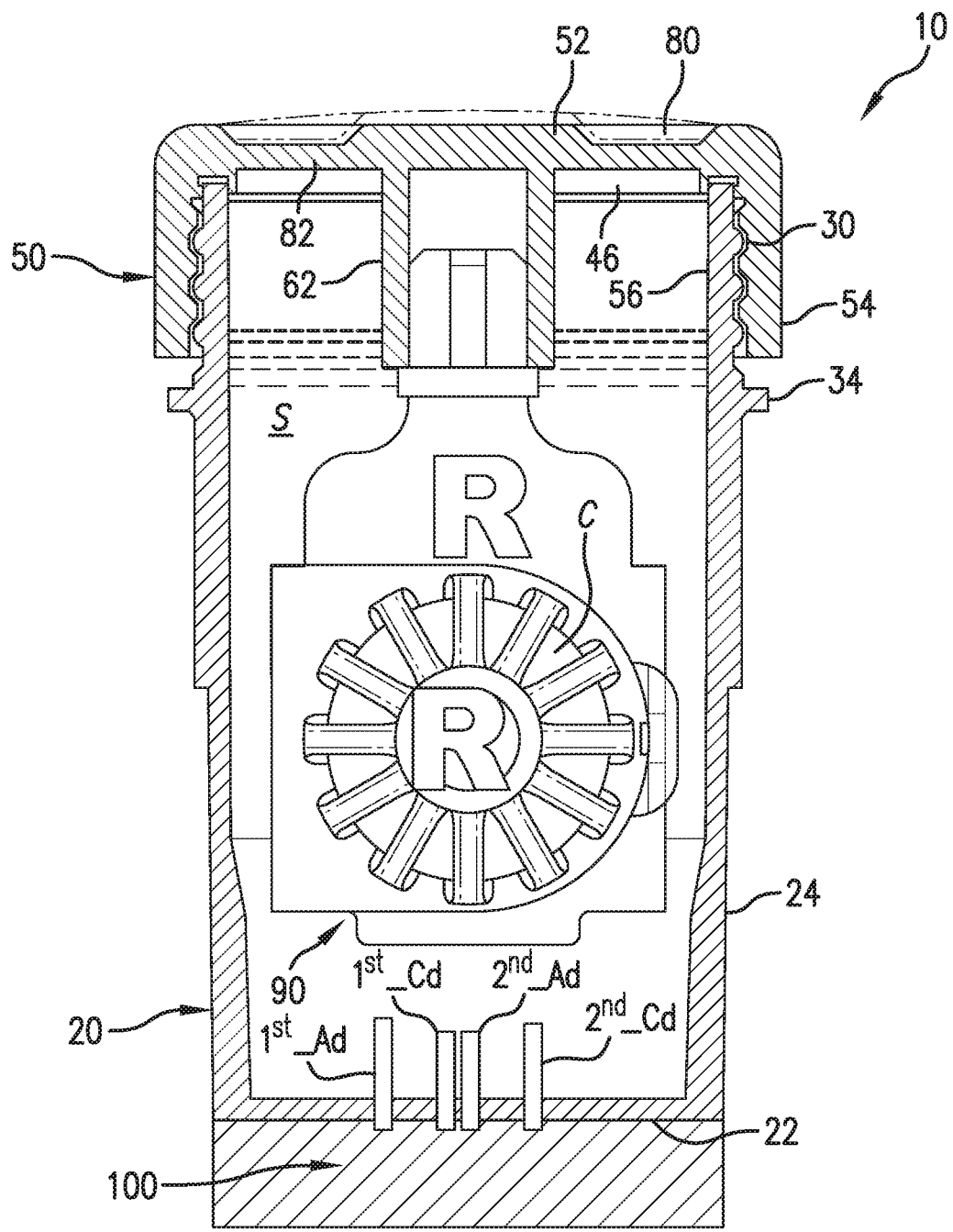
FIG. 2B is a cross-sectional view of the lens care system of FIG. 2A in an assembled state.
Figure 2C:
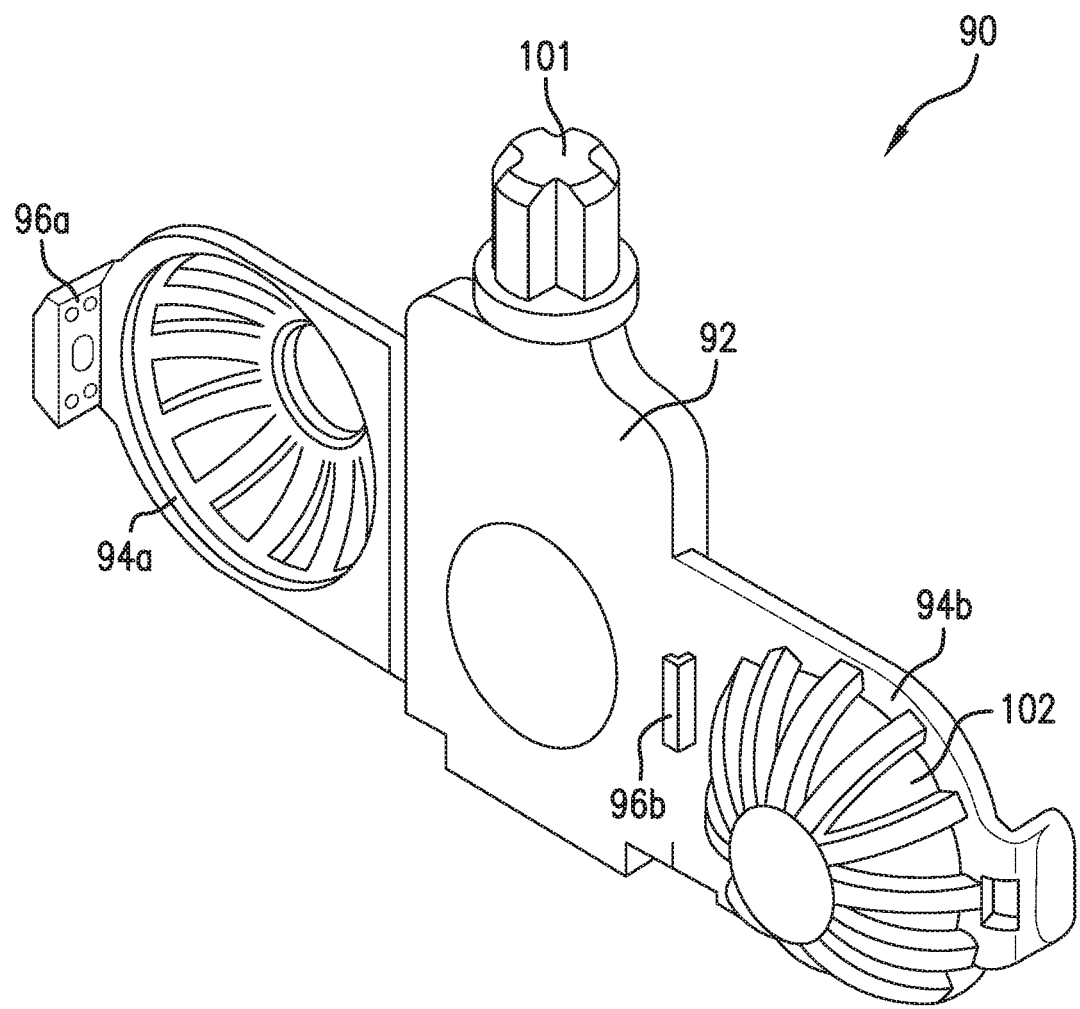
FIG. 2C is a perspective view of the contact lens holder component of the lens care system of FIG. 2A, with its lens retaining baskets shown in an open configuration.

FIGS. 2A-2C illustrate a preferred system 10 for cleaning, disinfecting and/or storing one or more contact lenses or other ophthalmic or medical devices. The lens care system 10 generally comprises a container cup 20, a cap 50 for removable attachment onto the container cup, a lens holder 90, and a control unit 100. FIG. 2A shows the components in a partially disassembled state; whereas FIG. 2B shows the assembled system in an example manner of use, with a contact lens C retained in the lens holder 90 and immersed in a liquid lens care solution S, and with the two pairs of electrodes $1^{st}\_Ad$, $2^{nd}\_Ad$, $1^{st}\_Cd$ and $2^{nd}\_Cd$ operatively connected to the control unit 100 and immersed in the liquid lens care solution S.

The container cup 20 is generally cylindrical, having a bottom panel 22 and a tubular sidewall 24 having a generally circular profile. The container cup defines an interior chamber accessible from an open top end bounded by a circumferential upper rim 26 opposite the bottom panel 22. One or more flats 28 or other surface features are optionally provided on the exterior surface of the sidewall 24 to provide improved grip for a user.

The four electrodes $1^{st}\_Ad$, $2^{nd}\_Ad$, $1^{st}\_Cd$ and $2^{nd}\_Cd$ are provided on the bottom panel 22 and are spaced to each other spaced apart from each other or as close as possible to each other. Any conventional inert electrically conductive material, e.g. platinum, graphite, palladium, aluminum, gold, silver, ruthenium, or boron doped diamond, or a conductive polymer, can be used in making the electrodes $1^{st}\_Ad$, $2^{nd}\_Ad$, $1^{st}\_Cd$ and $2^{nd}\_Cd$. In one preferred embodiment, the anode $2^{nd}\_Ad$ having a negatively-charged membrane thereon and the cathode $1^{st}\_Cd$ preferably are boron doped diamond electrodes and separated from each other merely by a negatively-charged membrane (not shown). It is understood that a liquid-tight seal should be formed between the electrodes and the bottom panel 22 of the container cup. It is further understood that the cathode $2^{nd}\_Cd$ can be removed from the system.

Alternatively, the four electrodes can be attached to the bottom of the lens holder and protrude downwardly from the lens holder or formed into the walls of the lens holder (not shown in the figures).

The control unit 100 comprises means (e.g., electronic circuitry) (not shown) for operatively connecting the electrodes with the power source (not shown) and microprocessors/embedded systems (not shown) for automatically controlling the electrode polarity and potential of the electrodes, as well as the timing and duration of the electrochemical neutralization process. The control unit 100 preferably also contains a power pack (AC or DC battery), an automatic switching mechanism, indicator means, etc. (not shown). The control unit 100 may be a separate unit from the container cup 20 and they may be connected to each other by cable or an interlocking socket arrangement. Alternatively, the control unit 100 may be permanently incorporated in the container cup 20 as an integral part of the bottom panel 22.

The container cup 20 is preferably a unitary component, for example integrally molded of polystyrene, polypropylene, polyethylene, ABS and/or other plastic or polymeric material(s) of construction, as by injection molding or other fabrication process. The container cup 20 comprises a first helical thread profile 30 on its exterior surface proximal the upper rim 26. The first threads 30 are optionally split by one or more unthreaded segments 32, providing a discharge channel for gas vented from the container during use, as will be described below. The unthreaded segment 32 preferably defines a gas venting channel extending generally linearly from the rim 26 of the container cup through the entire threaded portion of the cup, providing a passage for free discharge flow of pressurized gas therethrough from the container when the cap is assembled onto the cup. A circumferential cup flange 34 extends transversely outward from the exterior surface of the sidewall 24 beneath the thread profile 30.

The cap 50 comprises a generally circular top panel 52 and a circumferential collar 54 extending transversely downward from the top panel. The collar 54 has an inner diameter configured to receive the outer diameter of the container cup 20, preferably with a loose or free running fit. The interior face of the collar 54 comprises a second helical thread profile 56, which engages with the first thread profile 30 on the container cup 20 when the cap 50 is screwed onto the container cup to hold the components together in their assembled state. The second threads 56 are optionally split by one or more unthreaded segments, providing a discharge channel for gas vented from the container during use. Also, sufficient spacing or play is preferably provided between the first and second thread profiles to permit gas discharge through the threaded interface. The collar 54 optionally comprises one or more flats along its exterior circumference, forming a rounded polygonal profile, to provide improved grip for a user. The cap 50 is preferably a unitary component, for example integrally molded of polypropylene, polyethylene, polystyrene, ABS and/or other plastic or polymeric material(s) of construction, as by injection molding or other fabrication process.

A coupling hub 62 projects downward from the center of the interior face of the top panel 52 of the cap 50, and defines a central receiver for receiving a cooperating retention finger of the lens holder 90. A resilient cap sealing flange or lip 46 projects downward from the interior face of the top panel 52 of the cap 50. The lip 46 has a continuous circular profile extending proximal the outer periphery of the interior face of the top panel 52, and spaced inwardly from the threaded interior face of the collar 54 a distance generally corresponding to the wall thickness of the sidewall 24 of the container cup 20. In this manner, when the cap 50 is installed onto the container cup 20, the outer face of the lip 46 interfaces with the interior surface of the container cup along its rim 26 to form a continuous liquid-tight seal in the cap's undeformed state. The outer face of the lip 46 is optionally provided a slight inward taper, to provide a ring of sealing point contact at the edge formed by the intersection of the upper face of the rim 26 and the interior surface of the container cup. The lip 46 is preferably an integral part of the cap 50, rather than a separate component, such that a sealing and venting interface is formed between the cup and the cap with minimal complexity. In this manner, no separate washer or seal component is required to form a seal between the container cup and the cap. In alternate embodiments, the seal interface comprises separate seal and/or vent components attached to the cap and/or cup.

A spaced array of interference ribs (not shown) are optionally provided along the interior face of the top panel 52 between the lip 46 and the interior face of the collar 54, to prevent tightening the cap 50 to such an extent that the rim 26 of the container cup 20 would seal against the interior face of the cap's top panel to prevent discharge of gas from the container. Alternatively, one or more recesses can be formed in the interior face of the top panel between the cap's lip and the interior face of its collar to allow gas discharge. Seating of the interference ribs on the interior face of the cap's top panel against the rim 26 of the container cup 20 defines the position of the cap relative to the container cup when the container is closed, and this seating location is controlled to provide a specified degree of interference or compression between the tapered contact face of the cap's sealing lip 46 against the container cup's rim. For example, control of the diameter of the sealing lip 46 and the height of the interference ribs to provide a seal interference of about 25 µm-50 µm between the sealing lip of the cap with the rim of the container cup may provide a suitable releasable seal interface.

The top panel 52 of the cap 50 has an annular channel or ring-shaped recess or depression 80 formed in its upper or exterior surface. This channel 80 results in a circular section or web 82 of decreased material thickness around the periphery of the top panel 52. The outer periphery of the section of reduced thickness 82 on the exterior surface of the top panel 52 is generally aligned with and opposite the position of the sealing lip 46 on the interior surface of the top panel. The material of construction of the cap 50 and the thickness and location of this section 82 are specified in conjunction to result in a top panel 52 configuration that allows a degree of flexure of the top panel in response to a threshold pressure within the container. For example, the cap 50 may comprise a polypropylene such as Huntsman/FHR P5M6K-048 polymer, and the web 82 of decreased material thickness have a thickness of between about 0.75 mm-1.75 mm, for example about 1.25 mm, and a diametral span of about 20 mm-30 mm, for example about 25 mm. When a threshold pressure of for example 1-8 pounds per square inch (psi) is reached, the top panel deforms or bulges outwardly from its undeformed state (shown in solid lines in FIG. 2B) into a deformed state (shown in broken lines in FIG. 2B), causing the lip 46 to tilt inwardly and out of contact with the rim 26 of the container cup. Pressurized gas within the contained volume defined by the cup 20 and attached cap 50 may then escape or vent through the threaded interface of the cup and cap, and/or though the gas venting channel formed by the unthreaded segment 32 of the threaded coupling between the container cup and the cap, if present. Because no separate seal or washer component is interposed between the container cup and the cap, the released gas discharges directly between the cap and the container cup, without passing through any intermediate seal chamber or cavity. Release of the excess gas reduces the pressure within the contained volume back below the threshold pressure, and the top panel returns to its undeformed state biased by the cap material's resilience or shape memory. During the cleaning and disinfecting process, continuing gas generation may result in an intermittent sequence or cycle of increasing pressure and venting or "burping" to release excess gas. The resilience of the cap 50 maintains the circular lip 46 of the cap 50 in sealing contact with the rim 26 of the container cup 20 except when venting excess gas, thereby preventing leakage of liquid from the container. In alternate embodiments, the top panel of the cap comprises various other configurations allowing for controlled flexure or deformation and release of excess internal pressure. For example, a recessed section could be formed on the interior and/or exterior surface(s) of the top panel, a plurality of ribs of varying flexure may be formed on the top panel, and/or a series of stepped indentations or rings may be formed on the top panel.

The lens holder 90 is shown in detail in its open state in FIG. 2C and in its closed state in FIG. 2A. The lens holder comprises a body panel 92 having first and second lens basket panels 94a, 94b attached thereto by an integral or living hinge formed by a web of reduced material thickness. Interengaging clips or closure members 96a, 96b are provided for holding the lens basket panels in their closed state, and releasing with finger pressure to allow insertion and removal of a lens from the basket. A retention finger 101 extends from an upper end of the body panel 92. The retention finger 101 optionally defines a cross-shaped profile for stability. The retention finger 101 has an outer periphery configured to form an interference or clearance fit within the receiver of the coupling hub 62 of the cap 50 as shown in FIG. 2B. The basket panels 94 are perforated with a plurality of slots or openings 102 to allow lens care solution to flow therethrough.

In use, the container 10 is opened by unscrewing the cap 50 from the container cup 20. A lens care solution is dispensed into the container cup 20 to a desired fill level. One or more contact lenses are placed in the lens holder 90 between the body panel and the basket panels, and the basket panels are closed and clasped. The retention finger of the lens holder is inserted into the receiver of the cap's hub. The lens holder and lenses are inserted into the container cup and immersed in the lens care solution. The cap is screwed onto the container cup to close the container, bringing the sealing lip of the cap into sealing interface with the rim of the container cup to prevent liquid leakage, and activating the control unit. As the cleaning and disinfecting process progresses, gases formed by electrolysis will generates a positive pressure differential within the contained volume of the system, relative to the external atmosphere. When this internal pressure reaches a threshold pressure, the top panel of the cap flexes or deforms, disengaging the sealing interface between the lip of the cap and the rim of the container cup. Excess gas is released between the cap lip and cup rim, over the cup rim between the interference ribs, and through the threaded interface between the first and second thread profiles and/or through the unthreaded segments of the split threads. As the gas is released, the pressure drops below the threshold pressure, and the cap flexes back to its undeformed state, sealing the cap lip and cup rim against leakage. The sequence of pressure build-up and release continues until the cleaning and disinfecting process is complete.

After the contact lenses are immersed in the lens care solution containing electrolytically-generated germicide species for a disinfecting period of time (preferably at least about one hour, more preferably from about 2 hour to about 6 hours, even more preferably from about 3 hours to about 5 hours) sufficient to disinfect the contact lens, the control unit switches on the power and applies a potential to a different pair of electrodes, starting the electrochemical neutralization process of germicide species. The control unit will turn off the power after a desired period of time sufficient to reduce the concentration of hypochlorous acid and hypochlorite to less than 1 ppm (preferably about 0.5 ppm or less, more preferably about 0.1 ppm or less, even more preferably about 0.01 ppm or less).

After the neutralization of germicide species, the lenses may continue to be stored in the container, or removed by unscrewing the cap from the container cup. The system is preferably reusable, and the used lens care solution can be disposed of and the process repeated.

Any aqueous lens care solutions can be used in the invention, so long as it contains chloride ions. An aqueous lens care solution used in this invention comprises from about 0.30% to about 1.4% (preferably from about 0.5% to about 1.2%, more preferably from about 1.0%) by weight of one or more chloride salts (e.g., sodium chloride, potassium chloride, or both) and has a pH of from about 6 to about 8 (preferably from about 6.5 to about 7.5, more preferably from about 6.8 to about 7.2) and a tonicity of from about 150 to about 400 mOsm/kg (preferably from about 200 to about 350 mOsm/kg, more preferably from about 250 to about 350 mOsm/kg) at 25° C.

A person skilled in the art knows well how to adjust the tonicity of an aqueous solution with a tonicity agent. Besides chloride salts (e.g., sodium chloride and potassium chloride), other suitable occularly acceptable tonicity agents known to a person skilled in the art can be used in adjusting the tonicity of the lens care solution. Preferred examples of other tonicity agents include, without limitation, sodium sulfate, potassium sulfate, glycerol, propylene glycol, polyethylene glycols, polios, mannitols, sorbitol, xylitol and mixtures thereof.

An aqueous lens care solution of the invention is formulated to have a pH within a physiologically acceptable range of from about 6.0 to about 8.0, preferably from about 6.5 to about 7.5, more preferably from about 6.8 to about 7.2. The pH of the aqueous lens care solution of the invention preferably comprises one or more buffer selected from inorganic or organic bases, preferably basic acetates, phosphates, borates, citrates, nitrates, sulfates, tartrates, lactates, carbonates, bicarbonates and mixtures thereof, more preferably basic phosphates, borates, citrates, tartrates, carbonates, bicarbonates and mixtures thereof. Typically, it is present in an amount of 0.001% to 2%, preferably 0.01% to 1%; most preferably from about 0.05% to about 0.30% by weight.

The buffer component preferably includes one or more phosphate buffers, for example, combinations of monobasic phosphates, dibasic phosphates and the like. Particularly useful phosphate buffers are those selected from phosphate salts of alkali and/or alkaline earth metals. Examples of suitable phosphate buffers include one or more of sodium dibasic phosphate ($Na_2HPO_4$), sodium monobasic phosphate ($NaH_2PO_4$), and potassium monobasic phosphate ($KH_2PO_4$).

In accordance with the invention the aqueous lens care solution preferably further comprises a surfactant for cleaning the contact lens. Any suitable known surfactants can be used in the invention. Examples of suitable surfactants include, but are not limited to homopolymers of polyethylene glycol or polyethyleneoxide, poloxamers under the tradename Pluronic from BASF Corp. (Pluronic™ and Pluronic-R™) which are nonionic surfactants consisting of block copolymers of propylene oxide and ethylene oxide; poloxamine which is a block copolymer derivative of ethylene oxide and propylene oxide combined with ethylene diamine; tyloxapol, which is 4-(1,1,3,3-tetramethylbutyl) phenol polymer with formaldehyde and oxirane; ethoxylated alkyl phenols, such as various surface active agents available under the tradenames TRITON (Union Carbide, Tarrytown, N.Y., USA) and IGEPAL (Rhone-Poulenc, Cranbury, N.J., USA); polysorbates such as polysorbate 20, including the polysorbate surface active agents available under the tradename TWEEN (ICI Americas, Inc., Wilmington, Del., USA.); alkyl glucosides and polyglucosides such as products available under the tradename PLANTAREN (Henkel Corp., Hoboken, N.J., USA); and polyethoxylated castor oils commercially available from BASF under the trademark CREMAPHOR; and combinations thereof.

Preferred surfactants include polyoxypropylene-polyoxyethylene-polyoxypropylene block copolymers, poly(oxyethylene)-poly(oxybutylene) block copolymers disclosed in U.S. Pat. No. 8,318,144 (incorporated herein by reference in its entirety), certain poloxamers such as materials commercially available from BASF under the tradenames PLURONIC® surfactants, and combinations thereof. Examples of PLURONIC® surfactants include: PLURONIC® L42, PLURONIC® L43, and PLURONIC® L61. Examples of PLURONIC® R surfactants include: PLURONIC® 31R1, PLURONIC® 31R2, PLURONIC® 25R1, PLURONIC® 17R1, PLURONIC® 17R2, PLURONIC® 12R3, PLURONIC® 17R4, PLURONIC® F-68NF, PLURONIC® F68LF, and PLURONIC® F127. Examples of poly(oxyethylene)-poly(oxybutylene) block copolymers include di-block copolymer, denoted as PEO-PBO (i.e., polyoxyethylene-polyoxybutylene), a tri-block copolymer, represented as PEO-PBO-PEO or PBO-PEO-PBO, or other block-type configurations. When present, surfactants may be employed at a concentration of from about 0.005% to about 1% by weight, preferably from about 0.01% to about 0.5% by weight, more preferably from about 0.02% to about 0.25% by weight, even more preferably from about 0.04% to about 0.1% by weight, based on the total amount of aqueous lens care solution.

In a preferred embodiment, an aqueous lens care solution of the invention further comprises a polyoxypropylene-polyoxyethylene-polyoxypropylene block copolymer in an amount of from about 0.005% to about 1% by weight, preferably from about 0.01% to about 0.5% by weight, more preferably from about 0.02% to about 0.25% by weight, even more preferably from about 0.04% to about 0.1% by weight, based on the total amount of aqueous lens care solution.

In another preferred embodiment, an aqueous lens care solution of the invention further comprises a poly(oxyethylene)-poly(oxybutylene) block copolymer, in an amount of from about 0.005% to about 1% by weight, preferably from about 0.01% to about 0.5% by weight, more preferably from about 0.02% to about 0.25% by weight, even more preferably from about 0.04% to about 0.1% by weight, based on the total amount of aqueous lens care solution.

As used in this application, a poly(oxyethylene)-poly(oxybutylene) block copolymer may be in the form of a di-block copolymer, denoted as PEO-PBO, a tri-block copolymer, represented as PEO-PBO-PEO or PBO-PEO-PBO, or other block-type configurations.

In accordance with this preferred embodiment, the poly(oxyethylene)-poly(oxybutylene) block copolymers utilized in the present invention have a weight average molecular weight in the range of from about 400 to about 1200 Daltons; and more preferably in the range of from about 700 to about 900 Daltons.

In another preferred embodiment, an aqueous lens care solution of the invention further comprises a homopolymer or copolymer of vinylpyrrolidone, in an amount of from about 0.02% to about 5% by weight, preferably 0.1 to 3%; more preferably from about 0.5% to about 2%, most preferably from about 0.25% to about 1.5% by weight, based on the total amount of aqueous lens care solution.

In accordance with this preferred embodiment of the invention, any copolymers of vinylpyrrolidone and at least one hydrophilic monomer can be used in this invention. A preferred class of copolymers is the copolymers of vinyloyrrolidone and at least one amino-containing vinylic monomer. Examples of amino-containing vinylic monomers include without limitation alkylaminoalkylmethacrylate having 8-15 carbon atoms, alkylaminoalkylacrylate having 7-15 carbon atoms, dialkylaminoalkylmethacrylate having 8-20 carbon atoms, dialkylaminoalkylacrylate having 7-20 carbon atoms, N-vinylalkylamide having 3-10 carbon atoms. Examples of preferred N-vinyl alkylamide include without limitation N-vinyl formaide, N-vinyl acetamide, N-vinyl isopropylamide, and N-vinyl-N-methyl acetamide. Examples of preferred copolymers includes without limitation copolymers of vinylpyrrolidone and dimethylaminoethylmethacrylate. Such preferred copolymers are commercially available, e.g., Copolymer 845 and Copolymer 937 from ISP.

An aqueous lens care solution of the invention is preferably formulated in such a way that it has a viscosity of about 0.8 centipoise to about 15 centipoises at 25° C., preferably from about 0.8 centipoises to about 10 centipoises at 25° C., more preferably from about 0.8 centipoises to about 1.1 centipoises at 25° C. It is known to a person skilled in the art how to adjust the viscosity of an aqueous solution by using one or more viscosity-enhancing agents.

In accordance with the invention, an aqueous lens care solution of the invention can further comprise from about 0.002% to about 0.5% by weight, more preferably from about 0.004% to about 0.1% by weight, even more preferably from about 0.005% to about 0.05% by weight of one or more components selected from the group consisting of lubricant(s), conditioning/wetting agent(s), antimicrobial agent(s), chelating agent(s), defoaming agents, microbicide (s), preservative(s), and combinations thereof, based on the total amount of aqueous lens care solution.

A lens care solution of the invention preferably comprises a lubricant. "Lubricants" as used herein refer to any compounds or materials which can enhance surface wettability of a contact lens and/or the eye or reduce the friction character of the contact lens surface. Examples of lubricants include without limitation mucin-like materials and hydrophilic polymers.

Exemplary mucin-like materials include without limitation polyglycolic acid, polylactides, collagen, and gelatin. A mucin-like material may be used to alleviate dry eye syndrome. The mucin-like material preferably is present in effective amounts.

Exemplary hydrophilic polymers include, but are not limited to, polyvinylalcohols (PVAs), polyamides, polyimides, polylactone, a homopolymer of a vinyl lactam, a copolymer of at least one vinyl lactam in the presence or in the absence of one or more hydrophilic vinylic comonomers, a homopolymer of acrylamide or methaacrylamide, a copolymer of acrylamide or methacrylamide with one or more hydrophilic vinylic monomers, mixtures thereof.

An aqueous lens care solution of the invention can also comprise one or more conditioning/wetting agents (e.g., polyvinyl alcohol, polyoxamers, polyvinyl pyrrolidone, hydroxypropyl cellulose, and mixture thereof).

An aqueous lens care solution of the invention may include an antimicrobial agent in an amount effective to preserve the aqueous lens care solution. The term "an amount effective to preserve" means an amount of an antimicrobial agent effective in producing the desired effect of preserving the solutions described herein from microbial contamination, preferably an amount which, either singly or in combination with one or more additional antimicrobial agents, is sufficient to satisfy the preservative efficacy requirements of the United States Pharmacopoeia ("USP"). In a preferred embodiment, an aqueous lens care solution comprises about 100 ppm or less, preferably about 75 ppm or less, more preferably about 60 ppm or less, even more preferably about 50 ppm or less of a peroxide compound selected from the group consisting of hydrogel peroxide, sodium perborate tetrahydrate, sodium percarbonate, sodium persulfate, and combinations thereof.

An aqueous lens care solution of the invention may include (but preferably does not include) an effective amount of a chelating agent. Any suitable, preferably ophthalmically acceptable, chelating agents may be included in the present compositions, although ethylenediaminetetraacetic acid (EDTA), salts thereof and mixtures thereof are particularly effective. EDTA is low level non-irritating chelating agent and can be synergistic with PHMB to increase antimicrobial efficacy. Typical amount of EDTA is from about 0.002% to about 0.5% by weight, more preferably from about 0.004% to about 0.1% by weight, even more preferably from about 0.005% to about 0.05% by weight, based on the total amount of aqueous lens care solution.

An aqueous lens care solution of the invention is produced in known manner, in particular, by means of conventional mixing of the constituents with water or dissolving the constituents in water.

The present invention, in another aspect, provides a method for disinfecting and cleaning contact lenses which are suitable for direct insertion into the eye upon completion of disinfection. A method of the invention comprises the steps of: (1) immersing a contact lens in an aqueous lens care solution including which comprises from about 0.30% to about 1.4% (preferably from about 0.5% to about 1.2%, more preferably from about 0.7% to about 1.0%) by weight of one or more chloride salts (e.g., sodium chloride, potassium chloride, or both) and has a pH of from about 6 to about 8 (preferably from about 6.5 to about 7.5, more preferably from about 6.8 to about 7.2) and a tonicity of from about 150 to about 400 mOsm/kg (preferably from about 200 to about 350 mOsm/kg, more preferably from about 250 to about 350 mOsm/kg) at 25° C.; (2) electrochemically generating germicide species in the aqueous lens care solution by using a first anode and a first cathode for a first period of time for disinfecting the contact lenses; (3) after the first period of time and optionally a disinfecting period of time, electrochemically neutralizing the germicide species which are generated electrochemically in step (2) and left-over from disinfecting of the contact lenses in the aqueous lens care solution, wherein the step of electrochemically neutralizing the germicide species is carried out by using a second anode and the first cathode or a second cathode, wherein the second anode has a negatively-charged membrane thereon for preventing a negatively charged ion from accessing the second anode.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part or can be combined in any manner and/or used together, as illustrated below:

1. A lens care apparatus for disinfecting contact lenses, comprising:
   (1) a container for holding an aqueous lens care solution having a pH of from about 6 to about 8 and comprising from about 0.30% to about 1.4% by weight of one or more halide salts (e.g., sodium chloride, potassium chloride, sodium bromide, potassium bromide, sodium iodide potassium iodide, or mixtures thereof), preferably chloride salts (e.g., sodium chloride, potassium chloride, or both) and a tonicity of from about 150 to about 400 mOsm/kg at 25° C., wherein the container comprises a container cup defining an interior chamber accessible through an opening bounded by a rim and for receiving the aqueous lens care solution, a cap for removable attachment onto the container cup to cover the opening, and a lens holder for retaining the contact lenses immersed in the aqueous lens care solution in the container cup;
   (2) a set of electrodes which are located in the interior chamber and immersed in the aqueous lens care solution when in use, wherein the set of electrodes comprises a first anode free of any negatively-charged membrane thereon, a second anode having a negatively charged membrane thereon for preventing a negatively charged ion from accessing the second anode, a first cathode, and optionally a second cathode; and
   (3) and a control unit operatively connected to the set of electrodes and to a power source, wherein the control unit automatically applies a first potential between the first anode and the first cathode and drives an electrical current through the first anode and the first cathode for a first period of time to electrochemically generate germicide species including halogen (e.g., chlorine, bromine or iodine, preferably chlorine), hypohalous acid (e.g., hypochlorous acid, hypobromous acid or hypoiodous acid, preferably hypochlorous acid), hypohalorite (e.g., hypochlorite, hypobromite or hypoiodite, preferably hypochlorite), or combinations thereof for disinfecting the contact lenses, and after the first period of time and optionally a disinfecting period of time for disinfecting contact lenses with the electrochemically generated germicide species, automatically applies a second potential between the second anode and the first or second cathode and drives an electrical current through the second anode and the first or second cathode for a second period of time to electrochemically neutralizing germicide species which are generated electrochemically but left-over from disinfecting of the contact lenses.

2. The lens care apparatus according to embodiment 1, wherein the aqueous lens care solution has a pH of from about 6.5 to about 7.5 (from about 6.8 to about 7.2).

3. The lens care apparatus according to embodiment 1 or 2, wherein the aqueous lens care solution has a tonicity of from about 200 to about 350 mOsm/kg (preferably from about 250 to about 350 mOsm/kg) at 25° C.

4. The lens care apparatus according to embodiment 1, 2 or 3, wherein the aqueous lens care solution comprises from about 0.5% to about 1.2% (preferably from about 0.7% to about 1.0%) by weight of one or more halide salts selected from the group consisting of sodium chloride, potassium chloride, sodium bromide, potassium bromide, sodium iodide potassium iodide, and mixtures thereof.

5. The lens care apparatus according to any one of embodiments 1 to 4, wherein the aqueous lens care solution comprises from about 0.5% to about 1.2% (preferably from about 0.7% to about 1.0%) by weight of one or more chloride salts selected from the group consisting of sodium chloride, potassium chloride, and both.

6. The lens care apparatus according to any one of embodiments 1 to 5, wherein the set of electrodes comprises a second cathode.

7. The lens care apparatus according to embodiment 6, wherein the second anode and the second cathode are separated merely by a negatively-charged membrane.

8. The lens care apparatus according to any one of embodiments 1 to 7, wherein the second anode and the first cathode are separated merely by a negatively-charged membrane.

9. The lens care apparatus according to any one of embodiments 1 to 8, wherein the first anode and the first cathode, is made of mesh of an electrically conductive material to increase its surface area for electrolysis.

10. The lens care apparatus according to any one of embodiments 1 to 9, wherein the first anode and the first cathode, is made of mesh of an electrically conductive material to increase its surface area for electrolysis and are applied onto inside walls of the interior chamber of the cup of the container at or near the bottom.

11. The lens care apparatus according to any one of embodiments 1 to 10, wherein the lens holder comprises one or more closable baskets, which open to receive the contact lenses to be disinfected and cleaned and close to retain the lenses during treatment.

12. The lens care apparatus according to any one of embodiments 1 to 11, wherein the control unit comprises means for operatively connecting the electrodes with the power source and microprocessors/embedded systems for automatically controlling the polarity and potential of the electrodes, and the timing and duration of processes for electrochemically generating germicide species, for disinfecting contact lenses with the electrochemically generated germicide species, and for electrochemically neutralizing germicide species.

13. The lens care apparatus according to any one of embodiments 1 to 12, wherein the control unit comprises a power pack (AC or DC battery), an automatic switching mechanism, indicator means, or combinations thereof.

14. A method for disinfecting and cleaning contact lenses which are suitable for direct insertion into the eye upon completion of disinfection, comprising the steps of:
   (1) immersing a contact lens in an aqueous lens care solution including which comprises from about 0.30% to about 1.4% by weight of one or more halide salts selected from the group consisting of sodium chloride, potassium chloride, sodium bromide, potassium bromide, sodium iodide potassium iodide, and mixtures thereof and has a pH of from about 6 to about 8 and a tonicity of from about 150 to about 400 mOsm/kg at 25° C.;

(2) electrochemically generating germicide species in the aqueous lens care solution by using a first anode and a first cathode for a first period of time for disinfecting the contact lenses;

(3) after the first period of time and optionally a disinfecting period of time, electrochemically neutralizing the germicide species which are generated electrochemically in step (2) and left-over from disinfecting of the contact lenses in the aqueous lens care solution, wherein the step of electrochemically neutralizing the germicide species is carried out by using a second anode and the first cathode or a second cathode, wherein the second anode has a negatively-charged membrane thereon for preventing a negatively charged ion from accessing the second anode.

15. The method according to embodiment 14, wherein the aqueous lens care solution has a pH of from about 6.5 to about 7.5 (from about 6.8 to about 7.2).

16. The method according to embodiment 14 or 15, wherein the aqueous lens care solution has a tonicity of from about 200 to about 350 mOsm/kg (preferably from about 250 to about 350 mOsm/kg) at 25° C.

17. The method according to embodiment 14, 15 or 16, wherein the aqueous lens care solution comprises from about 0.5% to about 1.2% (preferably from about 0.7% to about 1.0%) by weight of one or more halide salts selected from the group consisting of sodium chloride, potassium chloride, sodium bromide, potassium bromide, sodium iodide potassium iodide, and mixtures thereof.

18. The method according to any one of embodiments 14 to 17, wherein the aqueous lens care solution comprises from about 0.5% to about 1.2% (preferably from about 0.7% to about 1.0%) by weight of one or more chloride salts selected from the group consisting of sodium chloride, potassium chloride, and both.

19. The method according to any one of embodiments 14 to 18, wherein the aqueous lens care solution has a volume in the range of from about 5 ml to about 15 ml (preferably from 7.5 ml to about 12.5 ml, more preferably from about 9 ml to about 11 ml).

20. The method according to any one of embodiments 14 to 19, wherein the aqueous lens care solution comprises at least one member selected from the group consisting of a polyoxypropylene-polyoxyethylene-polyoxypropylene block copolymer, a poly(oxyethylene)-poly(oxybutylene) block copolymer, a poly(oxyethylene)-poly(oxybutylene) di-block copolymer, a poly(oxyethylene)-poly(oxybutylene)-poly(oxyethylene) tri-block copolymer, a poly(oxybutylene)-poly(oxyethylene)-poly(oxybutylene) tri-block copolymer, a homopolymer of vinylpyrrolidone, a copolymer of vinylpyrrolidone and at least one amino-containing vinylic monomer having 8-15 carbon atoms.

The previous disclosure will enable one having ordinary skill in the art to practice the invention. In order to better enable the reader to understand specific embodiments and the advantages thereof, reference to the following non-limiting examples is suggested. However, the following examples should not be read to limit the scope of the invention.

Example 1

This example illustrates that hypochlorite can be reduced directly.

A.

A 100 ppm formulation of sodium hypochlorite (diluted from 5%, Ricca, into solution buffered with 0.53% boric acid, 0.05% sodium borate decahydrate, 0.59% sodium acetate). This solution was placed in a 3.5 ml cuvette, which was placed in a UV spectrometer. The amount of hypochlorite in solution can be monitored by measuring the absorbance at 291 nm. Prior to experimentation, the solution was verified to be greater than 10 ppm free and total chlorine using hypochlorite test strip (the upper limit for the test strips-Hach AquaCheck strips)

A pair of platinum wires were placed in the cuvette (~10 mm surface depth, or area 17.3 $mm^2$), and 150 mA was applied to the wires. Hypochlorite does decrease, to less than 20 ppm in 80 minutes (see FIG. 1, Curve 2). As a check, the solution was tested with chlorine strips, which resulted in 4 ppm of total chlorine, and 0.5 ppm free chlorine.

B.

Figure 3:
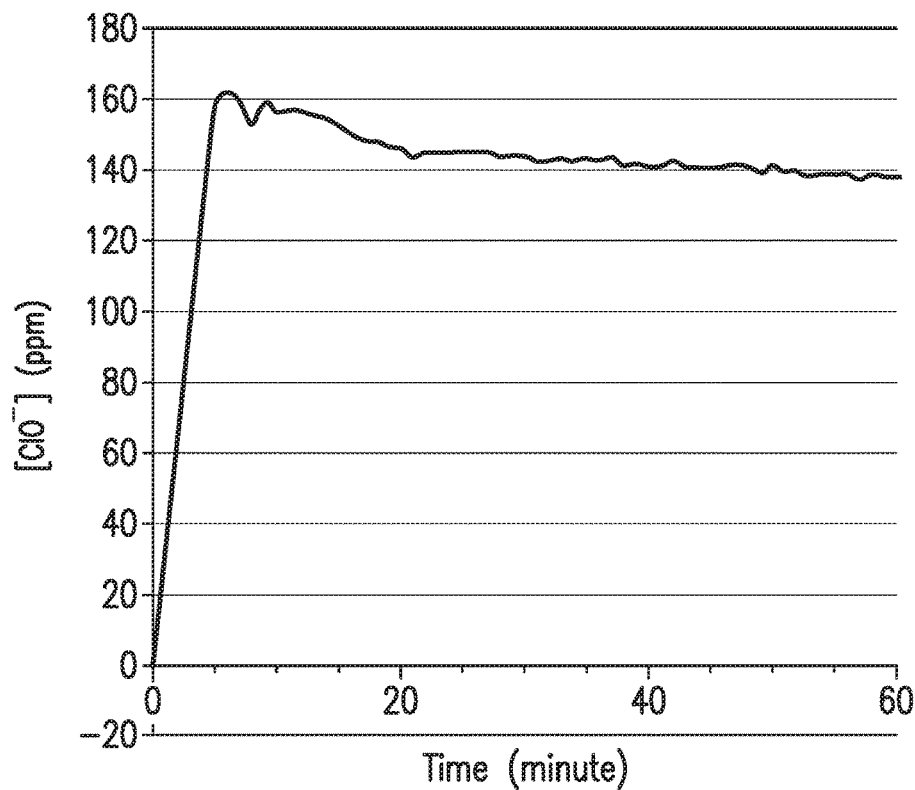
FIG. 3 shows hypochlorite formation from phosphate-buffered saline (0.83% NaCl) in a lens care system comprising a pair of boron-doped diamond electrodes, 5 minutes for 150 mA.

In another experiment, 100 ppm of sodium hypochloride (made with same buffer system as above) was added to a lens care system similar to an ozone-generating system (disclosed in US2012205255), in which a Clear Care® cup is retrofitted into the ozone-based system of US2012205255 by cutting the bottom of the Clear Care® cup. The system comprises a pair of boron-doped diamond electrodes (FIG. 3 of US2012205255) which are separated by a Nafion membrane (a negatively charged membrane and are held in place by a plastic frame. A UV probe is able to monitor the reaction during the reduction, as shown below. The 100 ppm hypochloride is reduced to safe levels (<1 ppm) within 20 minutes (FIG. 1, Curve 1). Both total and free chlorine measured 0 ppm after 30 minutes of treatment.

C.

In another experiment, ozone solution was prepared by using an ozone-generating system (FIGS. 1A-1D) disclosed in US2012205255) and then was transferred into a container holding 100 ppm hypochloride (10 ml). No reduction in hypochloride was seen with the bubbled ozone (FIG. 1, Curve 3).

Example 2

Ten ml of phosphate buffered saline (0.83% sodium chloride) was added to the lens care system described in Example 1B, and 150 mA was applied for 5 minutes. UV analysis of hypochlorite formation (as measured at 294 nm) indicated that the level of hypochloride exceeds 140 ppm in 5 minutes (see FIG. 3).

Example 3

Figure 4:
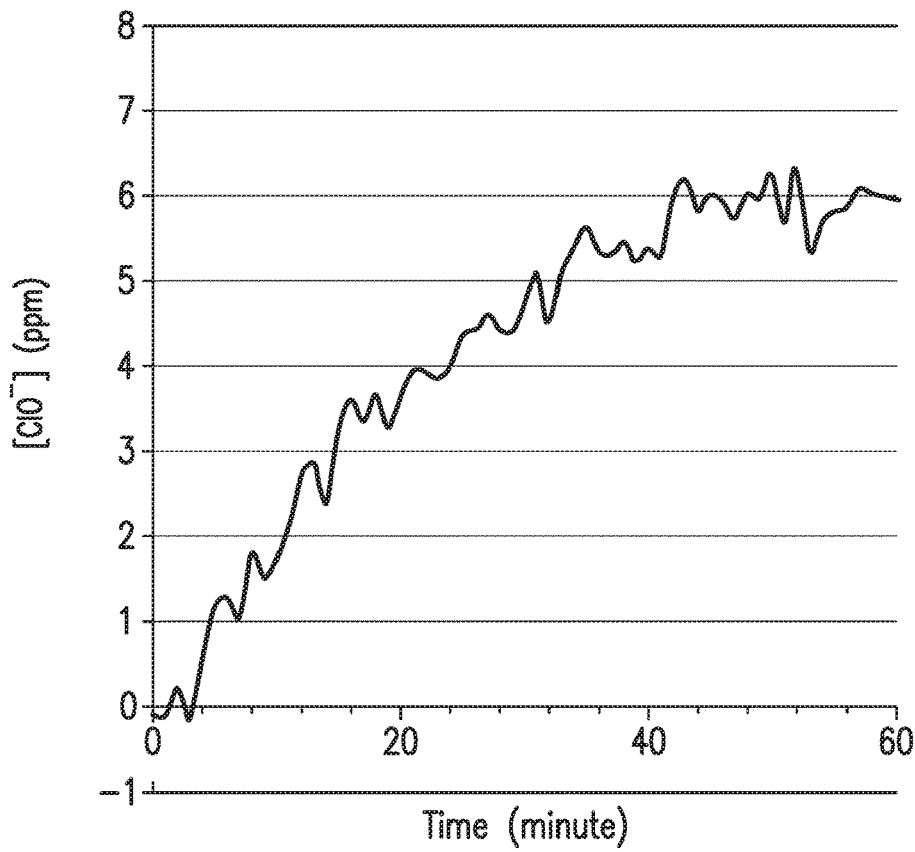
FIG. 4 shows hypochlorite formation from 3 mL of a 300 ppm NaCl solution with a buffer system (0.53% boric acid, 0.05% sodium borate decahydrate, 0.59% sodium acetate) in a cuvette with platinum wire electrodes (~ 10 mm surface depth, or area 17.3 mm2) to which a 4 V voltage is applied to provide 10 mA.

A 300 ppm NaCl formulation, 3.5 ml (made in same buffer system as example 1A) was added to a cuvette. A 4 V voltage is applied to provide 10 mA to the solution with platinum wire electrodes (~10 mm surface depth, or area 17.3 $mm^2$) shows about 6 ppm hypochloride in about 50 minutes (see FIG. 4). Chlorine strips indicate that approximately 1 ppm total free chlorine is present.

What is claimed is:

1. A lens care apparatus for disinfecting contact lenses, comprising:

(1) a container for holding an aqueous lens care solution, wherein the aqueous lens care solution has a pH of from about 6 to about 8 and comprises from about 0.5% to about 1.2% by weight of one or more chloride salts selected from the group consisting of sodium chloride, potassium chloride, and mixtures thereof, wherein the container comprises a container cup, a cap, and a lens holder, wherein the container cup is cylindrical and has a bottom panel and a tubular side wall defining an interior chamber accessible through an opening bounded by a circumferential upper rim opposite the bottom panel, wherein the container cup comprises first threads on the exterior surface of the container cup proximal to the upper rim, wherein the cap comprises a circular top panel and a circumferential collar extending transversely downward from the top panel, wherein the collar comprises second threads on the interior surface of the collar for engaging with the first threads on the container cup when the cap is screwed onto the container cup to close the container, wherein the lens holder comprises closable baskets and is attached to the interior surface of the top panel of the cap for inserting the lens holder into the container cup and for retaining the contact lenses immersed in the aqueous lens care solution in the container cup when the container is closed and is in use;

(2) a set of electrodes which are located in the interior chamber and on the bottom panel and immersed in the aqueous lens care solution when in use, wherein the set of electrodes comprises a first anode free of any negatively-charged membrane thereon, a second anode which is coated with a negatively charged membrane for preventing a negatively charged ion from accessing the second anode, a first cathode, and optionally a second cathode, wherein the second anode is a boron doped diamond electrode; and (3) a control unit operatively connected to the set of electrodes and to a power source, wherein the control unit automatically applies a first potential between the first anode and the first cathode and drives an electrical current through the first anode and the first cathode for a first period of time to electrochemically generate germicide species which are chlorine, hypochlorous acid, hypochlorite, or combinations thereof for disinfecting the contact lenses, and after the first period of time and optionally a disinfecting period of time for disinfecting contact lenses with the electrochemically generated germicide species, automatically applies a second potential between the second anode and the first or second cathode and drives an electrical current through the second anode and the first or second cathode for a second period of time to electrochemically neutralize germicide species which are generated electrochemically but left-over from disinfecting of the contact lenses.

2. The lens care apparatus of claim 1, wherein the set of electrodes comprises a second cathode.

3. The lens care apparatus of claim 2, wherein the closable baskets open to receive the contact lenses to be disinfected and cleaned and close to retain the lenses during treatment.

4. The lens care apparatus of claim 3, wherein the control unit comprises means for operatively connecting the electrodes with the power source and microprocessors/embedded systems for automatically controlling the polarity and potential of the electrodes, and the timing and duration of processes for electrochemically generating germicide species, for disinfecting contact lenses with the electrochemically generated germicide species, and for electrochemically neutralizing germicide species.

5. The lens care apparatus of claim 4, wherein the control unit comprises a power pack, an automatic switching mechanism, or combinations thereof.

6. The lens care apparatus of claim 1, wherein the closable baskets open to receive the contact lenses to be disinfected and cleaned and close to retain the lenses during treatment.

7. The lens care apparatus of claim 1, wherein the control unit comprises means for operatively connecting the electrodes with the power source and microprocessors/embedded systems for automatically controlling the polarity and potential of the electrodes, and the timing and duration of processes for electrochemically generating germicide species, for disinfecting contact lenses with the electrochemically generated germicide species, and for electrochemically neutralizing germicide species.

8. The lens care apparatus of claim 7, wherein the control unit comprises a power pack, an automatic switching mechanism, or combinations thereof.

9. The lens care apparatus of claim 8, wherein the control unit comprises means for operatively connecting the electrodes with the power source and microprocessors/embedded systems for automatically controlling the polarity and potential of the electrodes, and the timing and duration of processes for electrochemically generating germicide species, for disinfecting contact lenses with the electrochemically generated germicide species, and for electrochemically neutralizing germicide species.

10. The lens care apparatus of claim 1, wherein the control unit comprises a power pack, an automatic switching mechanism, or combinations thereof.

* * * * *